(12) United States Patent
Ellingson et al.

(10) Patent No.: US 8,260,422 B2
(45) Date of Patent: Sep. 4, 2012

(54) IMPLANTABLE MEDICAL DEVICE WITH SELECTIVELY CONFIGURABLE EXPOSURE OPERATING MODE PROGRAMMING OPTIONS

(75) Inventors: Michael L. Ellingson, St. Louis Park, MN (US); Hyun J. Yoon, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 354 days.

(21) Appl. No.: 12/581,433

(22) Filed: Oct. 19, 2009

(65) Prior Publication Data
US 2011/0093040 A1 Apr. 21, 2011

(51) Int. Cl.
*A61N 1/362* (2006.01)
(52) U.S. Cl. .......................................................... 607/30
(58) Field of Classification Search ................ 607/9, 30, 607/31, 59
See application file for complete search history.

(56) References Cited

U.S. PATENT DOCUMENTS

| | | | |
|---|---|---|---|
| 3,678,937 A | 7/1972 | Cole et al. | |
| 4,091,818 A | 5/1978 | Brownlee et al. | |
| 5,292,342 A | 3/1994 | Nelson et al. | |
| 5,438,990 A | 8/1995 | Wahlstrand et al. | |
| 5,529,578 A | 6/1996 | Struble | |
| 5,697,958 A | 12/1997 | Paul et al. | |
| 5,722,998 A | 3/1998 | Prutchi et al. | |
| 6,198,972 B1 | 3/2001 | Hartlaub et al. | |
| 6,348,070 B1 | 2/2002 | Teissl et al. | |
| 6,580,947 B1 | 6/2003 | Thompson | |
| 6,662,050 B2 | 12/2003 | Olson | |
| 6,901,292 B2 | 5/2005 | Hrdlicka et al. | |
| 6,925,328 B2 | 8/2005 | Foster et al. | |
| 6,937,906 B2 | 8/2005 | Terry et al. | |
| 7,024,249 B2 | 4/2006 | Weisner et al. | |
| 7,047,074 B2 | 5/2006 | Connelly et al. | |
| 7,076,283 B2 | 7/2006 | Cho et al. | |
| 7,082,328 B2 | 7/2006 | Funke | |

(Continued)

FOREIGN PATENT DOCUMENTS
EP 1493460 1/2005
(Continued)

OTHER PUBLICATIONS (PCT/US2010/031236) PCT Notification of Transmittal of the International Search Report and the Written Opinion of the International Searching Authority, Mailed Jul. 21, 2010, 12 pages.

*Primary Examiner* — George Evanisko
(74) *Attorney, Agent, or Firm* — Stephen W. Bauer; Michael J. Ostrom

(57) ABSTRACT

An IMD is selectively configurable to support a plurality of programming options for enabling and disabling an exposure operating mode of the device. In one example, the IMD may support at least two of a manual exposure mode programming option in which the exposure operating mode is manually enabled and manually disabled, an automatic exposure mode programming option in which the exposure operating mode is automatically enabled and automatically disabled, or a semi-automatic exposure mode programming option in which the exposure operating mode is either automatically enabled and manually disabled or manually enabled and automatically disabled. In this manner, the IMD may support more than one way for enabling and disabling the exposure operating mode to provide flexibility in the clinical workflows associated with programming the IMD into an exposure operating mode for a medical procedure, such as an MRI scan.

19 Claims, 9 Drawing Sheets

U.S. PATENT DOCUMENTS

| | | |
|---|---|---|
| 7,212,863 B2 | 5/2007 | Strandberg |
| 7,242,981 B2 | 7/2007 | Ginggen |
| 7,369,898 B1 | 5/2008 | Kroll et al. |
| 7,450,996 B2 | 11/2008 | MacDonald et al. |
| 7,546,157 B1 | 6/2009 | Kil et al. |
| 7,561,915 B1 | 7/2009 | Cooke et al. |
| 7,672,726 B2 * | 3/2010 | Ginggen .................. 607/27 |
| 2003/0083570 A1 | 5/2003 | Cho et al. |
| 2003/0144704 A1 | 7/2003 | Terry et al. |
| 2003/0144705 A1 * | 7/2003 | Funke .................. 607/27 |
| 2004/0088012 A1 | 5/2004 | Kroll et al. |
| 2005/0038482 A1 | 2/2005 | Yonce et al. |
| 2006/0167496 A1 | 7/2006 | Nelson et al. |
| 2006/0173295 A1 | 8/2006 | Zeijlemaker |
| 2006/0293591 A1 | 12/2006 | Wahlstrand et al. |
| 2007/0173890 A1 | 7/2007 | Armstrong |
| 2007/0238975 A1 | 10/2007 | Zeijlemaker |
| 2008/0147135 A1 | 6/2008 | Hareland |
| 2008/0154342 A1 | 6/2008 | Digby et al. |
| 2009/0157146 A1 | 6/2009 | Linder et al. |

FOREIGN PATENT DOCUMENTS

| | | |
|---|---|---|
| EP | 1 935 450 A1 | 6/2008 |
| WO | WO 2005035048 | 4/2005 |
| WO | WO 2006081434 | 8/2006 |
| WO | WO 2007117835 | 10/2007 |

* cited by examiner

IMPLANTABLE MEDICAL DEVICE WITH SELECTIVELY CONFIGURABLE EXPOSURE OPERATING MODE PROGRAMMING OPTIONS

TECHNICAL FIELD

The disclosure relates generally to implantable medical devices and, in particular, to the selectable configuration of an exposure operating mode of an implantable medical device.

BACKGROUND

A wide variety of implantable medical devices (IMDs) that deliver a therapy to and/or monitor a physiologic condition of a patient have been clinically implanted or proposed for clinical implantation in patients. IMDs may deliver therapy or monitor conditions with respect to a variety of organs, nerves, muscles or tissues of the patients, such as the heart, brain, stomach, spinal cord, pelvic floor or the like. In some cases, IMDs may deliver electrical stimulation therapy via one or more electrodes, which may be included as part of one or more elongated implantable medical leads.

For example, an implantable cardiac device, such as a cardiac pacemaker or implantable cardioverter-defibrillator, provides therapeutic stimulation to the heart by delivering electrical therapy signals such as pulses or shocks for pacing, cardioversion, or defibrillation via electrodes of one or more implantable leads. As another example, a neurostimulator may deliver electrical therapy signals, such as pulses, to a spinal cord, brain, pelvic floor or the like, to alleviate pain or treat symptoms of any of a number of neurological or other diseases, such as epilepsy, gastroparesis, Alzheimer's, depression, obesity, incontinence and the like.

Exposure of the IMD to a disruptive energy field may result in improper operation of the IMD, damage to the IMD and/or damage to tissue adjacent to portions of the IMD. The IMD may be exposed to the disruptive energy field for any of a number of reasons. For example, one or more medical procedures may need to be performed on the patient within whom the IMD is implanted for purposes of diagnostics or therapy. For example, the patient may need to have a magnetic resonance imaging (MRI) scan, computed tomography (CT) scan, electrocautery, diathermy or other medical procedure that produces a magnetic field, electromagnetic field, electric field or other disruptive energy field.

The disruptive energy field may induce energy on one or more of the implantable leads coupled to the IMD. The IMD may inappropriately detect the induced energy on the leads as physiological signals. Alternatively, or additionally, the induced energy on the leads may result in the inability to correctly detect physiological signals. In either case, detection of the induced energy on the leads as physiological signals may result in the IMD delivering therapy when it is not desired or withholding therapy when it is desired. In other instances, the induced energy on the leads may result in stimulation or heating of the tissue and/or nerve site adjacent to the electrodes of the leads or adjacent to the housing of the IMD. Such heating may result in thermal damage to the tissue, thus possibly compromising pacing and sensing thresholds at the site.

SUMMARY

In general, this disclosure relates to operation of an implantable medical device (IMD) in a disruptive energy field. In particular, this disclosure describes an IMD that is selectively configurable to support a plurality of programming options for enabling and disabling an exposure operating mode of the device. In one example, the IMD may support at least two of a manual exposure mode programming option in which the exposure operating mode is manually enabled and manually disabled, an automatic exposure mode programming option in which the exposure operating mode is automatically enabled and automatically disabled, or a semi-automatic exposure mode programming option in which the exposure operating mode is either automatically enabled and manually disabled or manually enabled and automatically disabled.

The exposure mode programming option may be selectable by a user, e.g., a physician, based on physician preference, patient preference, resource availability, experience scanning patients with IMDs, clinical practice within or across geographies, or other factor. In this manner, the IMD supports more than one way for enabling and disabling the exposure operating mode to provide flexibility in the clinical workflows associated with programming the IMD into an exposure operating mode for a medical procedure, such as an MRI scan.

In one example, this disclosure is directed to an implantable medical device comprising a receiver to receive a communication from an external medical device and a processor that is selectively configurable to operate in accordance with a plurality of exposure mode programming options that each correspond to a different manner for enabling and disabling an exposure operating mode of the implantable medical device. The processor configures the implantable medical device to operate in one of the plurality of exposure mode programming options based on the received communication, enables the exposure operating mode in accordance with the selected exposure mode programming option and disables the exposure operating mode in accordance with the selected exposure mode programming option.

In another example, this disclosure is directed to a method comprising receiving a communication from an external medical device and configuring an implantable medical device to operate in one of a plurality of supported exposure mode programming options based on the received communication. Each of the supported exposure mode programming options corresponds to a different manner for enabling and disabling an exposure operating mode of the implantable medical device. The method further includes enabling the exposure operating mode in accordance with the supported exposure mode programming option and disabling the exposure operating mode in accordance with the supported exposure mode programming option.

In a further example, this disclosure is directed to an implantable medical device comprising means for receiving a communication from an external medical device and means for configuring an implantable medical device to operate in one of a plurality of supported exposure mode programming options based on the received communication. Each of the supported exposure mode programming options corresponds to a different manner for enabling and disabling an exposure operating mode of the implantable medical device. The device further includes means for enabling the exposure operating mode in accordance with the supported exposure mode programming option and means for disabling the exposure operating mode in accordance with the supported exposure mode programming option.

In another example, this disclosure is directed to a computer-readable medium comprising instructions that, when executed, cause an implantable medical device to receive a communication from an external medical device, configure an implantable medical device to operate in one of a plurality of supported exposure mode programming options based on the received communication, wherein each of the supported exposure mode programming options corresponds to a different manner for enabling and disabling an exposure operating mode of the implantable medical device, enable the exposure operating mode in accordance with the supported exposure mode programming option and disable the exposure operating mode in accordance with the supported exposure mode programming option.

The details of one or more examples are set forth in the accompanying drawings and the description below. Other features, objects, and advantages will be apparent from the description and drawings, and from the statements provided below.

DETAILED DESCRIPTION

Figure 1:
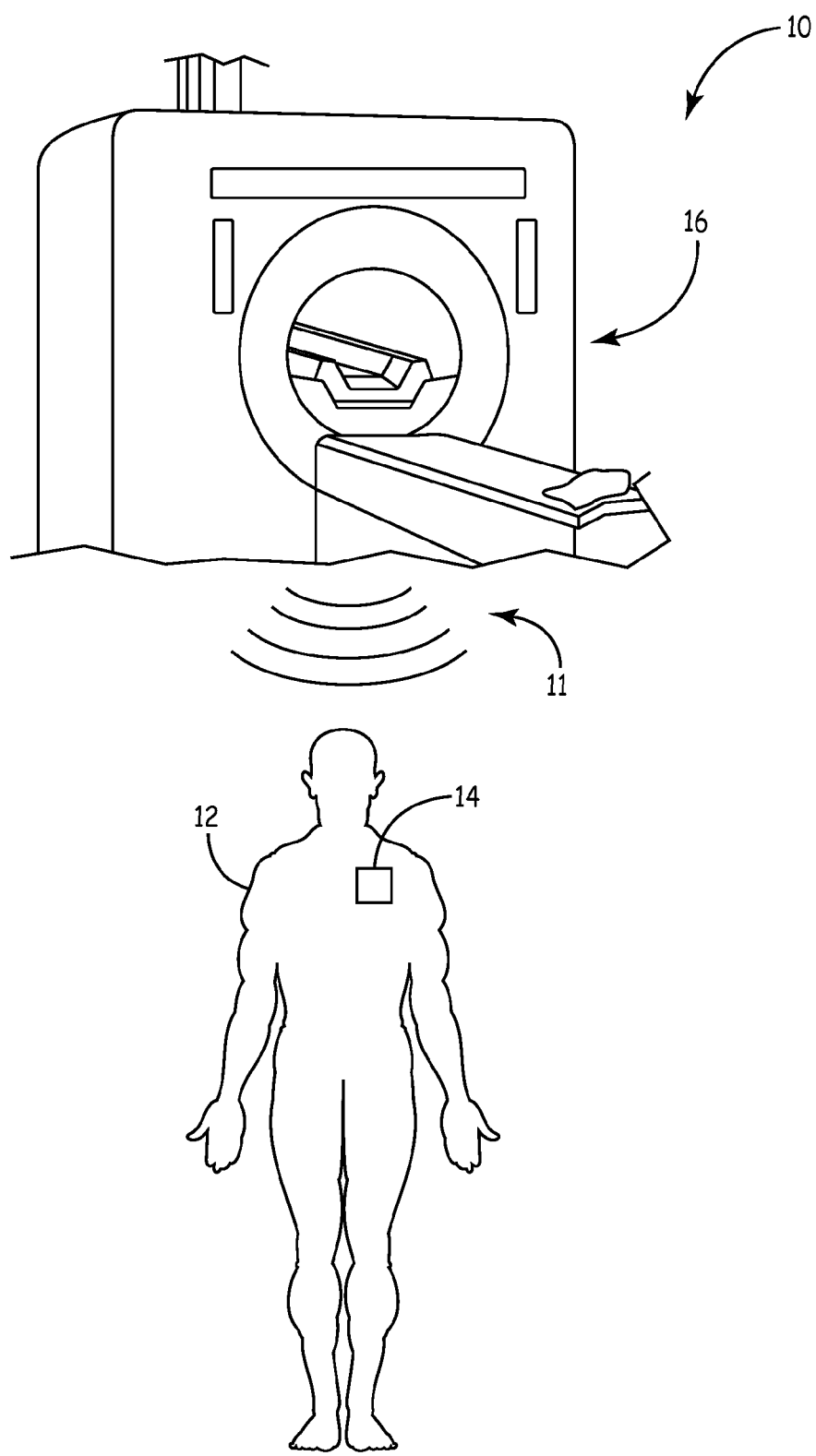
FIG. 1 is a conceptual diagram illustrating an environment in which an implantable medical device (IMD) is exposed to a disruptive energy field.

FIG. 1 is a conceptual diagram illustrating an environment 10 in which an implantable medical device (IMD) 14 is exposed to a disruptive energy field 11. IMD 14 is implanted within patient 12 to provide therapy to and/or to monitor a physiological condition of patient 12. The techniques, however, are not limited to devices implanted within patient 12. For example, the techniques may be used in conjunction with an external medical device that is adversely affected by disruptive energy field 11.

IMD 14 may be any of a variety of devices that provide therapy to patient 12, monitor a condition of patient 12, or both. For example, IMD 14 may be a device that provides electrical stimulation therapy via one or more implantable leads that include one or more electrodes (not shown in FIG. 1). In some instances, IMD 14 may be a device that provides electrical stimulation therapy in the form of cardiac rhythm management therapy to a heart of patient 12 via leads implanted within one or more atria and/or ventricles of the heart. In other instances, IMD 14 may be a device that provides electrical stimulation to a tissue site of patient 12 proximate a muscle, organ or nerve, such as a tissue proximate a vagus nerve, spinal cord, brain, stomach, pelvic floor or the like.

In addition to providing electrical stimulation therapy, IMD 14 may sense one or more physiological parameters of patient 12. When one or more leads are implanted within the heart of patient 12, for example, electrodes of the leads may sense electrical signals attendant to the depolarization and repolarizatoin of the heart to monitor a rhythm of the heart or detect particular heart conditions, e.g., tachycardia, bradycardia, fibrillation or the like. IMD 14 may sense a variety of other physiologic parameters or other parameters related to a condition of patient 12, including, for example, neurologic parameters, intracardiac or intravascular pressure, activity, posture, pH of blood or other bodily fluids or the like. In some instances, IMD 14 may be used solely for monitoring a condition of patient 12. In other words, IMD 14 may not provide therapy to patient 12, but simply sense a physiological or biological condition of patient 12.

In yet other instances, IMD 14 may be a device that delivers a drug or therapeutic agent to patient 12, e.g., via a catheter. IMD 14 may deliver, e.g., using a pump, the drug or therapeutic agent to a specific location of patient 12. IMD 14 may deliver the drug or therapeutic agent at a constant or variable flow rate. Drug pumps, infusion pump or drug delivery devices may be used to treat symptoms of a number of different conditions. For example, IMD 14 may deliver morphine or ziconotide to reduce or eliminate pain, baclofen to reduce or eliminate spasticity, chemotherapy to treat cancer, or any other drug or therapeutic agent (including saline, vitamins, etc.) to treat any other condition and/or symptom of a condition.

Environment 10 includes an energy source that generates disruptive energy field 11 to which IMD 14 is exposed. In the example illustrated in FIG. 1, the energy source is an MRI scanner 16. Although the techniques of this disclosure are described with respect to disruptive energy field 11 generated by MRI scanner 16, the techniques may be used to control operation of IMD 14 within environments in which other types of disruptive energy fields are present. For example, IMD 14 may operate in accordance with the techniques of this disclosure in environments in which disruptive energy field 11 is generated by a CT scanner, X-ray machine, electrocautery device, diathermy device, ablation device, radiation therapy device, electrical therapy device, magnetic therapy device, RFID security gate, or any other environment with devices that radiate energy to produce magnetic, electromagnetic, electric fields or other disruptive energy fields.

MRI scanner 16 uses magnetic and radio frequency (RF) fields to produce images of body structures for diagnosing injuries, diseases and/or disorders. In particular, MRI scanner 16 generates a static magnetic field, gradient magnetic fields and/or RF fields. The static magnetic field is a non-varying magnetic field that is typically always present around MRI scanner 16 whether or not an MRI scan is in progress. Gradient magnetic fields are pulsed magnetic fields that are typically only present while the MRI scan is in progress. RF fields are pulsed RF fields that are also typically only present while the MRI scan is in progress.

Some or all of the various types of fields produced by MRI scanner 16 may interfere with operation of IMD 14. In other words, one or more of the various types of fields produced by MRI scanner 16 may make up disruptive energy field 11. For example, the gradient magnetic and RF fields produced by MRI scanner 16 may induce energy on one or more of the implantable leads coupled to IMD 14. In some instances, IMD 14 inappropriately detects the induced energy on the leads as physiological signals, which may in turn cause IMD 14 to deliver undesired therapy or withhold desired therapy. In other instances, the induced energy on the leads result in IMD 14 not detecting physiological signals that are actually present, which may again result in IMD 14 delivering undesired therapy or withholding desired therapy. The induced energy on the leads may be delivered to the tissue of patient 12 resulting in stimulation or heating of the tissue and/or nerve site adjacent to electrodes of the leads. Such heating may cause thermal damage to the tissue adjacent the electrodes, possibly compromising pacing and sensing thresholds at the site. In yet other instances, the induced energy may cause damage to one or more components of IMD 14.

To reduce the undesirable effects of disruptive energy field 11, IMD 14 is capable of operating in a mode that is less susceptible to undesirable operation during exposure to disruptive energy field 11, referred to herein as the "exposure mode" or "exposure operating mode." Prior to being exposed or upon being exposed to disruptive energy field 11, IMD 14 is configured from a normal operating mode (e.g., the current operating mode) to the exposure operating mode.

In the normal operating mode, IMD 14 operates in accordance with all desired functionality using settings programmed by a physician, clinician or other user. When operating in the normal operating mode, IMD 14 may perform functions in a manner that does not specifically account for the presence of strong disruptive energy fields. The normal mode may correspond with the operating mode that a physician or other user feels provides a most efficacious therapy for patient 12. While operating in accordance with the normal operating mode, IMD 14 may sense physiological events, deliver a number of different therapies, and log collected data. In some instances, the normal operating mode may include a number of different operating modes that change based on a condition of the patient. However, the normal operating modes typically do not account for the presence of strong disruptive energy fields.

In the exposure mode, IMD 14 may perform functions in a manner that specifically accounts for the presence of strong disruptive energy fields. While operating in the exposure mode, IMD 14 may be configured to operate with different functionality than when operating in the normal operating mode. IMD 14 may, in some instances, be configured to operate with reduced functionality. In other words, when configured to operate in the exposure mode, IMD 14 may have only a subset of the functionality of the normal operating mode. For example, IMD 14 may not provide sensing, not deliver therapy, delivery only a subset of possible therapies, not log collected data or the like. In other instances, IMD 14 may be operating with approximately the same functionality or even increased functionality in the exposure mode. For example, IMD 14 may use a different sensor or algorithm to detect cardiac activity of the heart of patient 12, such as pressure sensor measurements rather than electrical activity of the heart.

The exposure operating mode of IMD 14 may be enabled and disabled in a number of different ways. For example, the exposure operating mode may be manually enabled and manually disabled, e.g., via communication with an external device, such as a programming device, a handheld activator or a home monitoring device. As another example, the exposure operating mode may be automatically enabled and automatically disabled, e.g., by detecting the MRI environment. In yet another example, the exposure operating mode may be automatically enabled and manually disabled or manually enabled and automatically disabled. In this case, the exposure operating mode may be viewed as being semi-automatic in that the exposure operating mode is either automatically enabled or disabled, but still requires some sort of manual intervention (e.g., the other of enabled or disabled).

In accordance with the techniques described in this disclosure, the manner in which the exposure operating mode of IMD 14 is enabled and disabled is selectively configurable. In other words, IMD 14 may support more than one way for enabling and disabling the exposure operating mode to provide flexibility in the clinical workflows associated with conducting an MRI scan of patient 12 or other medical or non-medical procedure in which IMD 14 is exposed to disruptive energy field 11. For example, IMD 14 may support two or more exposure mode programming options corresponding to different ways for enabling and disabling an exposure operating mode of the implantable medical device, e.g., a manual exposure mode programming option in which the exposure operating mode is enabled and disabled manually, an automatic exposure mode programming option in which the exposure operating mode is enabled and disabled automatically, a semi-automatic exposure mode programming option in which the exposure operating mode is automatically enabled and manually disabled and/or a semi-automatic exposure mode programming option in which the exposure operating mode is manually enabled and automatically disabled. As such, an appropriate exposure mode programming option may be selectable by a user, e.g., a physician, based on physician preference, patient preference, resource availability, experience scanning patients with IMDs, clinical practice within or across geographies, or other factor.

Although described with respect to a medical environment that generates disruptive energy fields, the techniques of this disclosure may be used to operate IMD 14 within non-medical environments that include disruptive energy fields. Additionally, the techniques of this disclosure may also be used to operate IMD 14 within environments that produce disruptive energy fields that are intermittent in nature.

Figure 2:
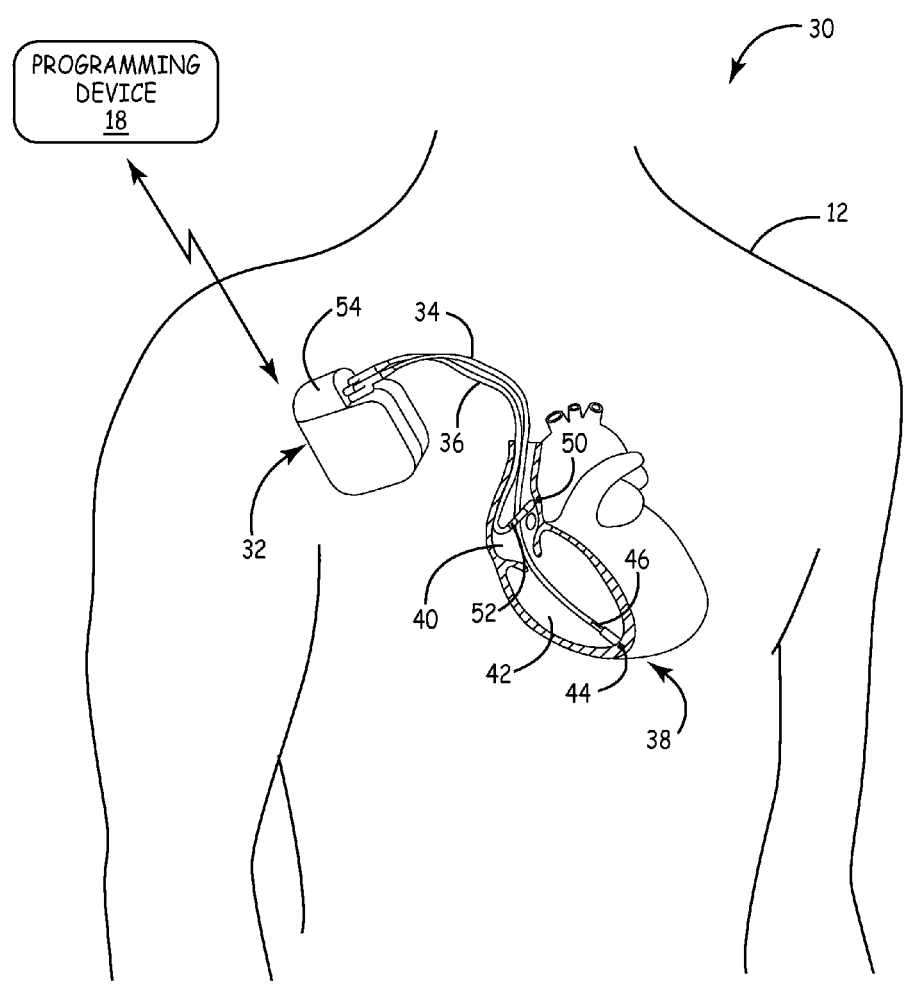
FIG. 2 is a conceptual diagram illustrating an example therapy system that may be used to provide therapy to a patient.

FIG. 2 is a conceptual diagram illustrating an example therapy system 30 that may be used to provide therapy to patient 12. Therapy system 30 includes an IMD 32 and leads 34 and 36 that extend from IMD 32. IMD 32 may, for example, correspond to IMD 14 of FIG. 1.

In the example illustrated in FIG. 2, IMD 32 is an implantable cardiac device that senses electrical activity of a heart 38 of patient 12 and/or provides electrical stimulation therapy to heart 38 of patient 12. The electrical stimulation therapy to heart 38, sometimes referred to as cardiac rhythm management therapy, may include pacing, cardioversion, defibrillation and/or cardiac resynchronization therapy (CRT). The combinations of cardiac therapies provided may be dependent on a condition of patient 12. In some instances, IMD 32 may provide no therapy to patient 12, but instead provide only sensing of electrical activity or other variable of heart 38, such as in the case of an implantable loop recorder.

In the illustrated example, lead 34 is a right ventricular (RV) lead that extends through one or more veins (not shown), the superior vena cava (not shown), and right atrium 40, and into right ventricle 42 of heart 38. Lead 34 includes electrodes 44 and 46 located along a distal end of lead 34. In the illustrated example, lead 36 is right atrial (RA) lead that extends through one or more veins and the superior vena cava, and into the right atrium 40 of heart 38. Lead 36 includes electrodes 50 and 52 located along a distal end of lead 36.

Electrodes 44 and 50 may take the form of extendable helix tip electrodes mounted retractably within an insulative electrode head (not shown) of respective leads 34 and 36. Electrodes 46 and 52 may take the form of ring electrodes. In other embodiments, electrodes 44, 46, 50 and 52 may be other types of electrodes. For example, electrodes 44, 46, 50 and 52 may all be ring electrodes located along the distal end of the associated lead 34 or 36. Additionally, either or both of leads 34 and 36 may include more than two electrodes or only a single electrode.

Each of the electrodes 44, 46, 50 and 52 may be electrically coupled to a respective conductor within the body of its associated lead 34 and 36. The respective conductors may extend from the distal end of the lead to the proximal end of the lead and couple to circuitry of IMD 32. For example, leads 34 and 36 may be electrically coupled to a stimulation module, a sensing module, or other modules of IMD 32 via connector block 54. In some examples, proximal ends of leads 34 and 36 may include electrical contacts that electrically couple to respective electrical contacts within connector block 54. In addition, in some examples, leads 34 and 36 may be mechanically coupled to connector block 54 with the aid of set screws, connection pins or another suitable mechanical coupling mechanism.

When IMD 32 is capable of delivering electrical stimulation therapy, IMD 32 delivers the therapy (e.g., pacing pulses) to heart 38 via any combination of electrodes 44, 46, 50 and 52 to cause depolarization of cardiac tissue of heart 38. For example, IMD 32 may deliver bipolar pacing pulses to right atrium 40 via electrodes 50 and 52 of lead 36 and/or may deliver bipolar pacing pulses to right ventricle 42 via electrodes 44 and 46 of lead 34. In another example, IMD 32 may deliver unipolar pacing pulses to atrium 40 and ventricle 42 using a housing electrode (not shown) in conjunction with one of electrodes 44, 46, 50 and 52. The housing electrode may be formed integrally with an outer surface of the hermetically-sealed housing of IMD 32 or otherwise coupled to the housing. In some examples, the housing electrode is defined by an uninsulated portion of an outward facing portion of the housing of IMD 32.

Electrodes 44, 46, 50 and 52 may also sense electrical signals attendant to the depolarization and repolarization of heart 38. The electrical signals are conducted to IMD 32 via one or more conductors of respective leads 34 and 36. IMD 32 may use any combinations of the electrodes 44, 46, 50, 52 or the housing electrode for unipolar or bipolar sensing. As such, the configurations of electrodes used by IMD 32 for sensing and pacing may be unipolar or bipolar depending on the application. IMD 32 may analyze the sensed signals to monitor a rhythm of heart 38 or detect an arrhythmia of heart 38, e.g., tachycardia, bradycardia, fibrillation or the like. In some instances, IMD 32 provides pacing pulses (or other therapy) to heart 38 based on the cardiac signals sensed within heart 38. In other words, pacing may be responsive to the sensed events.

As described above, exposure of IMD 32 to a disruptive energy field 11 (FIG. 1) may result in undesirable operation. For example, gradient magnetic and RF fields produced by MRI scanner 16 (FIG. 1) may induce energy on one or more of electrodes 44, 46, 50 and 52 of respective ones of implantable leads 34 and 36 or on the housing electrode. In some instances, IMD 32 inappropriately detects the induced energy on electrodes 44, 46, 50 and 52 as physiological signals, which may in turn cause IMD 32 to deliver undesired therapy or withhold desired therapy. In other instances, the induced energy on electrodes 44, 46, 50 and 52 result in IMD 32 not detecting physiological signals that are actually present, which may again result in IMD 32 delivering undesired therapy or withholding desired therapy. In further instances, the induced energy on electrodes 44, 46, 50 and 52 result in stimulation or heating of the tissue and/or nerve site adjacent to electrodes 44, 46, 50 and 52 or the housing of IMD 32. Such heating may result in thermal damage to the tissue adjacent the electrodes, possibly compromising pacing and sensing thresholds at the site. Yet another possible adverse effect of disruptive energy field 11 is damage to circuitry within IMD 32.

Configuring IMD 32 into an exposure operating mode may reduce, and possibly eliminate, the undesirable effects that may be caused by exposure to disruptive energy field 11. As such, IMD 32 may be configured to operate in the exposure operating mode prior to or immediately subsequent to entering the environment in which the disruptive energy field 11 is present. In accordance with the techniques described in this disclosure, the manner in which the exposure operating mode of IMD 32 is enable and disabled is selectively configurable. In other words, IMD 32 may support more than one way for enabling and disabling the exposure operating mode to provide flexibility in the clinical workflows associated with conducting an MRI scan of patient 12 or other medical or non-medical procedure in which IMD 32 is exposed to disruptive energy field 11.

A physician or other user may, for example, interact with a programming device 18 to select the manner in which the exposure operating mode of IMD 32 is enabled or disabled. For example, programming device 18 may include an electronic display via which programming device 18 presents the user with the programming options supported by IMD 32 for enabling and disabling the exposure operating mode. As described above, the programming options supported by IMD 32 may include a manual programming option in which the exposure operating mode is enabled and disabled manually, an automatic programming option in which the exposure operating mode is enabled and disabled automatically, a semi-automatic programming option in which the exposure operating mode is automatically enabled and manually disabled and/or a semi-automatic programming option in which the exposure operating mode is manually enabled and automatically disabled.

The user selects the desired programming option for enabling and disabling the exposure operating mode. The desired programming option selected by the user may be based on user preference, patient preference, resource availability, experience scanning patients with IMDs, clinical practice within or across geographies, or other factor. In response to the interaction of the user, programming device 18 transmits a communication to IMD 32 to configure IMD 32 to operate in accordance with the selected exposure mode programming option. IMD 32 receives the communication from programming device 18 and configures itself to the programming option specified in the communication. As such, IMD 32 is selectively configurable to different programming options for enabling and disabling the exposure operating mode.

In addition to configuring IMD 32 into the desired programming option for enabling and disabling the exposure operating mode, the user may interact with programming device 18 to select different settings within a particular programming option. For example, the user may interact with programming device 18 to select detection parameters for automatically enabling and/or disabling the exposure operating mode in the automatic programming option. Programming device 18 then transmits the selected settings of the particular programming option to IMD 32 in the communication along with the selected programming option or in a separate communication.

The user may further interact with programming device 18 to configure one or more parameters of the exposure operating mode. For example, the user may specify a pacing mode (e.g., atrial-based pacing mode, ventricular-based pacing mode or dual-chamber based pacing mode), pacing amplitude, pacing pulse width, and/or pacing rate of the therapy energy delivered during the exposure operating mode. Programming device 18 then transmits the selected settings of the particular programming option to IMD 32. Additionally, the user may interact with the programming device 18 to enable the exposure operating mode when utilizing the manual programming option or the semi-automatic programming option in which the exposure operating mode is manually enabled or manually disabled.

The user may interact with a programming device 18 to communicate with IMD 32 for other purposes than selecting the exposure mode programming option of IMD 32, manually enabling or disabling the exposure mode, or providing exposure mode operating parameters. For example, the user may interact with programming device 18 to retrieve physiological information, diagnostic information, logs of delivered therapies, or an assessment of the performance or integrity of IMD 32 or other components of therapy system 30, such as leads or a power source of IMD 32. Programming device 18 may transmit a communication requesting such information or receive the information without providing such a request.

The user may also interact with programming device 18 to program IMD 32, e.g., select values for operational parameters of the normal operating mode of IMD 32, such as a therapy progression, an electrode or combination of electrodes of leads 34 and 36 to use for delivering electrical stimulation (pulses or shocks), select parameters for the electrical pulse or shock (e.g., pulse amplitude, pulse width, or pulse rate), select electrodes or sensors for use in detecting a physiological parameter of patient 12, or the like. Programming device 18 may transmit a communication that includes the selected operational parameters of the normal operating mode.

Programming device 18 may communicate with IMD 32 via wireless communication using any techniques known in the art. Examples of communication techniques may include, for example, magnetic telemetry, low frequency telemetry or RF telemetry, but other techniques are also contemplated. In some instances, programming device 18 and IMD 32 may communicate in the 402-405 MHz frequency band in accordance with the Medical Implant Communications Service (MICS) frequency band regulation, in the 401-402 MHz or 405-406 MHz frequency bands in accordance with the Medical External Data Service (MEDS) band regulations, in the unlicensed industrial, scientific and medical (ISM) band, or other frequency band.

Programming device 18 may be a dedicated hardware device with dedicated software for programming of IMD 32. Alternatively, programming device 18 may be an off-the-shelf computing device running an application that enables programming device 18 to program IMD 32. In some examples, programming device 18 may be a handheld computing device or a computer workstation. Programming device 18 may, in some instances, include a programming head that may be placed proximate to the patient's body near the implant site of IMD 32 in order to improve the quality or security of communication between IMD 32 and programming device 18. Programming device 18 may include one or more processors, such as one or more microprocessors, digital signal processors (DSPs), application specific integrated circuits (ASICs), field-programmable gate arrays (FPGAs), programmable logic circuitry, or the like, that may perform various functions and operations, such as those described herein.

The configuration of therapy system 30 illustrated in FIG. 2 is merely an example. In other examples, therapy system 30 may include more or fewer leads extending from IMD 32. For example, IMD 32 may be coupled to three leads, e.g., a third lead implanted within a left ventricle of heart 30. In another example, IMD 32 may be coupled to a single lead that is implanted within either an atrium or ventricle of heart 38. As such, IMD 32 may be used for single chamber or multi-chamber cardiac rhythm management therapy.

In addition to more or fewer leads, each of the leads may include more or fewer electrodes. In instances in which IMD 32 is used for therapy other than pacing, e.g., defibrillation or cardioversion, the leads may include elongated electrodes, which may, in some instances, take the form of a coil. IMD 32 may deliver defibrillation or cardioversion shocks to heart 38 via any combination of the elongated electrodes and housing electrode. As another example, therapy system 30 may include leads with a plurality of ring electrodes, e.g., as used in some implantable neurostimulators.

In still other examples, a therapy system may include epicardial leads and/or patch electrodes instead of or in addition to the transvenous leads 34 and 36 illustrated in FIG. 2. Further, IMD 32 need not be implanted within patient 12. In examples in which IMD 32 is not implanted in patient 12, IMD 32 may deliver electrical stimulation therapy to heart 38 via percutaneous leads that extend through the skin of patient 12 to a variety of positions within or outside of heart 38.

The techniques of this disclosure are described in the context of cardiac rhythm management therapy for purposes of illustration. The techniques of this disclosure, however, may be used to operate an IMD that provides other types of electrical stimulation therapy. For example, the IMD may be a device that provides electrical stimulation to a tissue site of patient 12 proximate a muscle, organ or nerve, such as a tissue proximate a vagus nerve, spinal cord, brain, stomach, pelvic floor or the like. Moreover, the techniques may be used to operate an IMD that provides other types of therapy, such as drug delivery or infusion therapies. As such, description of these techniques in the context of cardiac rhythm management therapy should not be limiting of the techniques as broadly described in this disclosure.

Figure 3:
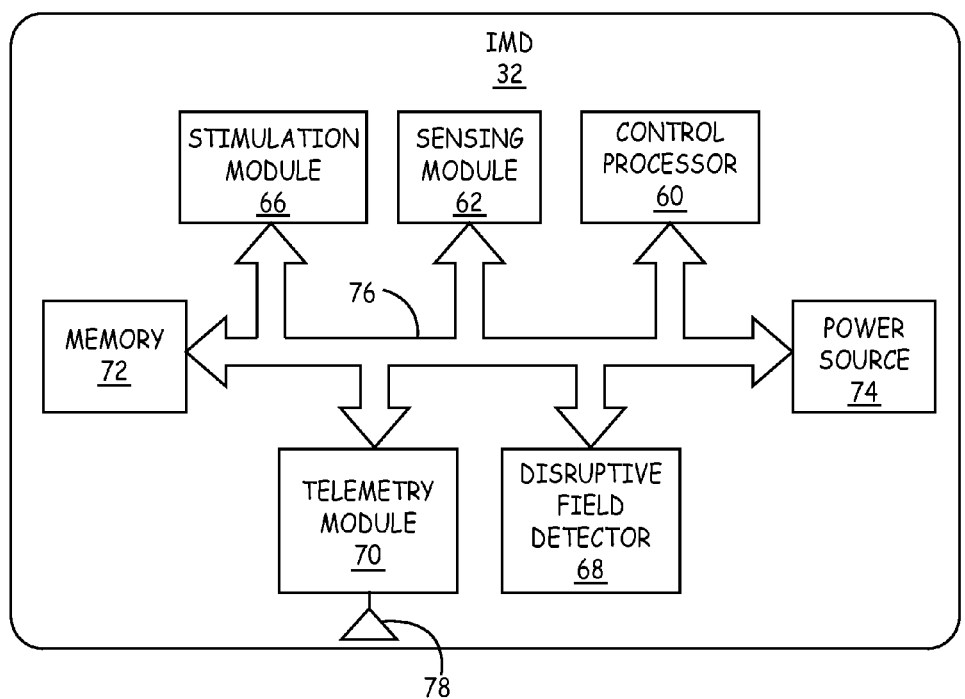
FIG. 3 is a functional block diagram of an example configuration of components of an IMD.

FIG. 3 is a functional block diagram of an example configuration of components of IMD 32. In the example illustrated by FIG. 3, IMD 32 includes a control processor 60, sensing module 62, stimulation module 66, disruptive field detector 68, telemetry module 70, memory 72 and power source 74, all of which are interconnected by a data bus 76.

As described above, IMD 32 is selectively configurable to support a plurality of programming options for enabling or disabling an exposure operating mode designed to perform functions of IMD 32 in a manner that specifically accounts for the presence of strong disruptive energy fields. Each of the programming options may correspond to a different manner of enabling and/or disabling exposure operating mode of IMD 32. For example, IMD 32 may support two or more of a manual programming option, an automatic programming option or a semi-automatic programming option. The manual programming option requires that a user manually enable and disable the exposure operating mode of IMD 32 using programming device 18 or other external device that is capable of communicating or otherwise activating IMD 32. Thus, IMD 32 is operating in the exposure operating mode from the time at which the mode is manually enabled until the time at which the mode is manually disabled.

In the automatic exposure mode programming option, IMD 32 enables and disables the exposure operating mode of IMD 32 in response to one or more conditions, e.g., detection of disruptive energy field 11 with disruptive field detector 68 (e.g., detection of the static magnetic field, the gradient magnetic fields or the RF pulses of MRI scanner 16), expiration of a timer, detection of some other signal, or other condition or a combination of conditions. The condition(s) for enabling and disabling the exposure operating mode may be the same for enabling and disabling the exposure operating mode or the condition(s) for enabling the exposure operating mode may be different than the condition(s) for disabling the exposure operating mode. For example, processor 60 may automatically configure IMD 32 to operate in accordance with the parameters of the exposure operating mode in response to disruptive field detector 68 detecting disruptive energy field 11 of MRI scanner 16 and automatically disable the exposure operating mode in response to disruptive field detector 68 no longer detecting disruptive energy field 11 of MRI scanner 16. As another example, processor 60 may automatically configure IMD 32 to operate in accordance with the parameters of the exposure operating mode in response to disruptive field detector 68 detecting disruptive energy field 11 of MRI scanner 16 and automatically disable the exposure operating mode after a predetermined period of time (e.g., one hour).

Processor 60 may automatically configure IMD 32 to enable and/or disable the exposure operating mode upon satisfaction of multiple conditions. The multiple conditions may be concurrent conditions or conditions that occur in a specific order. For example, processor 60 may automatically configure IMD 32 to operate in accordance with the parameters of the exposure operating mode in response to disruptive field detector 68 detecting disruptive energy field 11 of MRI scanner 16 within a particular time period (e.g., on a specified day and/or time) and automatically disable the exposure operating mode after no longer detecting disruptive energy field 11 for a particular period of time. These are just a few examples of the automatic programming option. Any combination of one or more conditions may be required for automatically enabling or disabling the exposure operating mode of IMD 32.

In the semi-automatic programming option, the user either manually enables the exposure operating mode of IMD 32 and processor 60 automatically disables the exposure operating mode of IMD 32 or processor 60 automatically enables the exposure operating mode of IMD 32 and the user manually disables the exposure operating mode of IMD 32. As with the automatic programming option, IMD 32 automatically enables or automatically disables the exposure operating mode of IMD 32 in response to one or a combination of conditions, such as the ones described in detail above.

IMD 32 may additionally be capable of supporting different settings within each of the exposure mode programming options. As one example, the user may selectively configure IMD 32 to specify the condition or conditions required to automatically enable and/or disable the exposure operating mode. The user may, for example, selectively configure IMD 32 to enable and/or disable the exposure operating mode using a timer, one or more disruptive field detectors 68, or a combination thereof. Additionally, the user may selectively configure thresholds for each of the selected conditions, e.g., threshold magnitudes of the detected fields, time periods for the timer or the like. As such, the exposure mode programming option of IMD 32 is not only selectively configurable, but so are settings within each of the exposure mode programming options.

Processor 60 of IMD 32 may receive a communication signal from programming device 18 or other external device indicating the programming option selected by a user, e.g., a physician. Processor 60 may store predetermined configuration settings for each of the programming options in memory 72 and select the configuration settings corresponding to the programming option indicated in the communication signal. The communication signal may, for example, indicate the programming option selected by the user in either the header or the body of the communication. Alternatively, the communication signal received by processor 60 may include the configuration settings for the programming option selected by the user.

Prior to enabling the exposure operating mode, e.g., either automatically or manually, processor 60 operates IMD 32 in accordance with settings programmed by a physician, clinician or other user, referred to herein as the normal operating mode. The normal operating mode may correspond with the operating mode that a physician or other user feels provides a most efficacious therapy for patient 12. The normal operating mode may vary from patient to patient depending on the condition of patient 12 for which IMD 32 is providing therapy. In some instances, the normal operating mode may be adaptive in that the normal operating mode actually includes switching between more than one pacing mode based on the condition of the patient, such as described in U.S. Pat. No. 7,130,683 to Casavant et al., entitled, "PREFERRED ADI/R: A PERMANENT PACING MODE TO ELIMINATE VENTRICULAR PACING WHILE MAINTAINING BACKUP SUPPORT," which issued on Oct. 31, 2006 and which is incorporated herein by reference in its entirety.

The normal operating mode of IMD 32 may be one or more of any of a number of pacing modes, including DDD, VVI, DVI, VDD, AAI, DDI, DDDR, VVIR, DVIR, VDDR, AAIR, DDIR, VOO, AOO, DOO, ODO and other modes of single and dual-chamber pacing or sensing. For example, the normal operating mode may be an atrial based pacing mode, such as AAI or ADI pacing mode, if IMD 32 is providing therapy to a patient experiencing bradycardia. As another example, the normal operating mode may be a dual-chamber pacing mode, such as a DDD pacing mode, if IMD 32 is providing therapy to a patient with unreliable A-V conduction.

In the aforementioned operating modes, the abbreviations of which conform to the NBG Pacemaker Code, the first letter in the pacing mode indicates the chamber or chambers paced and may take on the letter "D" indicating dual-chamber (i.e., atrial and ventricle both paced), "V" indicating a ventricle is paced, "A" indicating an atrium is paced, or "O" indicating no chamber is paced. The second letter indicates the chamber or chambers sensed and may take on the letter "D" indicating dual-chamber (i.e., atrial and ventricle both paced), "V" indicating a ventricle is paced, "A" indicating an atrium is paced, or "O" indicating no chamber is paced. The third letter indicates mode or modes of response to sensing and may take on the letter "T" indicating triggered pacing (i.e., pacing is provided in response to the sensing), "I" indicating inhibited pacing (i.e., pacing is stopped based in response to the sensing), "D" indicating dual response (i.e., triggered and inhibited) and "O" for no response. The fourth letter indicates programmable functions and may take on the letter "R" indicating rate modulated pacing, as well as other letters not explained here. Although not described here, a fifth letter may be provided in accordance with the NBG Pacemaker Code indicating anti-tachycardia functions.

When IMD 32 is configured to generate and deliver therapy to heart 38, control processor 60 controls stimulation module 66 to deliver electrical stimulation therapy to heart 38 via one or more of electrodes 44, 46, 50, 52 and/or the housing electrode. Stimulation module 66 is electrically coupled to electrodes 44, 46, 50 and 52, e.g., via conductors of the respective lead 34 and 36, or, in the case of the housing electrode, via an electrical conductor disposed within the housing of IMD 32. Control processor 60 controls stimulation module 66 to generate and deliver electrical pacing pulses with the amplitudes, pulse widths, rates, electrode combinations or electrode polarities specified by a selected therapy program. For example, electrical stimulation module 66 may deliver bipolar pacing pulses via ring electrodes 46 and 52 and respective corresponding helical tip electrodes 44 and 50 of leads 34 and 36, respectively. Stimulation module 66 may deliver one or more of these types of stimulation in the form of other signals besides pulses or shocks, such as sine waves, square waves, or other substantially continuous signals. In addition to pacing pulses, stimulation module 66 may, in some instances, deliver other types of electrical therapy, such as defibrillation therapy or cardioversion therapy.

Processor 60 may include a pacer timing and control module (not shown), which may be embodied as hardware, firmware, software, or any combination thereof. The pacer timing and control module may comprise a dedicated hardware circuit, such as an ASIC, separate from other components of control processor 60, or comprise a software module executed by a component of control processor 60, which may be a microprocessor or ASIC. In other instances, the pacer timing and control module may be part of stimulation module 66.

The pacer timing and control module may include programmable counters which control the basic time intervals associated with various single and dual-chamber pacing modes. Intervals defined by the pacer timing and control module within control processor 60 may include, for example, atrial and ventricular pacing escape intervals and refractory periods during which sensed atrial and ventricular events are ineffective to restart timing of the escape intervals. As another example, the pace timing and control module may define a blanking period, and provide signals to sensing module 62 to blank one or more channels, e.g., amplifiers, for a period during and after delivery of electrical stimulation to heart 38. The durations of these intervals may be determined by control processor 60 in response to parameters of the operating mode, which are stored in memory 72. The pacer timing and control module of control processor 60 may also determine the amplitude and pulse width of the cardiac pacing pulses.

During pacing, escape interval counters within the pacer timing and control module of control processor 60 may be reset upon sensing of R-waves and P-waves with detection channels of sensing module 62. Additionally, the value of the count present in the escape interval counters when reset by sensed R-waves and P-waves may be used by control processor 60 to measure the durations of R-R intervals, P-P intervals, P-R intervals and R-P intervals, which are measurements that may be stored in memory 72. Control processor 60 may analyze these various intervals to determine conditions of heart 38, such as to detect a tachyarrhythmia event. When IMD 32 is capable of providing defibrillation therapy, the R-R intervals may be used to increment a VF counter to control delivery of cardioversion or defibrillation shocks. For example, the VF counter may be incremented in response to detection of short R-R intervals, and possibly in response to other events such as R-R interval variance. The VF counter triggers delivery of a defibrillation shock when the counter reaches a number of intervals for detection (NID) threshold. Additionally, control processor 60 may begin an anti-tachyarrhythmia pacing regimen prior to delivery of the defibrillation shock.

Sensing module 62 is configured to receive signals from one or more sensors. In one example, sensing module 62 is configured to receive signals sensed by one or more of electrodes 44, 46, 50, 52 and the housing electrode. In this manner, electrodes 44, 46, 50, 52, and the housing electrode may operate as sense electrodes in addition to or instead of being used for delivering electrical stimulation therapy. In other instances, leads 34 and 36 may include one or more electrodes dedicated for sensing. In further examples, sensing module 62 is coupled to one or more sensors that are not included on leads 34 and 36, e.g., via a wired or wireless coupling. Such sensors may include, but are not limited to, pressure sensors, accelerometers, flow sensors, blood chemistry sensors, activity sensors or other type of physiological sensor. Signals monitored by sensing module 62 may be stored in memory 72.

Sensing module 62 may receive signals sensed by any number of sensing configurations defined by various combinations of one or more of electrodes 44, 46, 50 and 52. Control processor 60 may select the electrodes that function as sense electrodes, sometimes referred to as a sensing configuration or sensing vector, in order to monitor electrical activity of heart 38. In one example, sensing module 62 may include a switch module (not shown) to select which of the available electrodes are used to sense the heart activity. Control processor 60 may select the electrodes that function as sense electrodes, or the sensing electrode configuration, via the switch module within sensing module 62, e.g., by providing signals via a data/address bus.

Sensing module 62 may store the sensed signals in memory 72. In some instances, sensing module 62 may store the sensed signals in raw form. In other instances, sensing module 62 may process the sensed signals and store the processed signals in memory 72. Sensing module 62 may, for example, include multiple detection channels configured to detect different cardiac events, such as intrinsic or paced atrial events, intrinsic or paced ventricular events, repolarization of the ventricles, and the like. Each of the detection channels may comprise an amplifier, filter or other components. Sensing module 62 may amplify and filter the sensed signal and store the filtered signal in memory 72. The signals stored by sensing module 62 may, in some cases, be retrieved and further processed by control unit 60. In some instances, stimulation module 66 may be controlled by processor 60 based on the signals sensed by sensing module 62.

As described above, the normal operating mode of IMD 32 may be susceptible to undesirable operation when IMD 32 is placed within environment 10 with disruptive energy field 11. In some instances, sensing module 62 inappropriately detects the induced energy on the leads as physiological signals (e.g., intrinsic cardiac events). In other words, IMD 32 senses a physiological signal when one is not actually present. At the very least, the detection of the induced energy caused by disruptive energy field 11 results in the stored data not accurately representing the actual function and condition of heart 38. Moreover, the detection of the induced energy caused by disruptive energy field 11 may in turn cause undesirable operation of IMD 32.

For example, when the current or normal operating mode is a pacing mode with inhibit response to sensing, processor 60 may not deliver (i.e., withhold) a desired pacing pulse in response to sensing the induced energy from disruptive energy field 11 as a physiological signal. For example, processor 60 may identify the induced energy as a ventricular event. This may result in control processor 60 resetting the ventricular escape interval counter, thereby inhibiting delivery of a desired pacing pulse. In other instances when the normal operating mode is a dual chamber pacing mode with inhibit and trigger response to sensing, processor 60 may also deliver an undesirable pacing pulse in addition to withholding a desired pacing pulse in response to sensing the induced energy from disruptive energy field 11 as a physiological signal. In particular, sensing the induced energy from the disruptive energy field as a physiological signal may inappropriately start an escape interval after which an undesired pacing pulse is delivered. This may result in dangerously fast heart rhythms and may lead to tachyarrhythmia or fibrillation.

In other instances, the induced energy on the leads may result in IMD 32 not sensing actual physiological signals that are present. Processor 60 may, for example, initiate a blanking period in response to the induced energy on the leads. During the blanking period, sensing module 62 may power down one or more sense amplifiers. As such, sensing module 62 will fail to detect any intrinsic physiological event that occurs during the blanking period. Failure to detect this actual physiological event may again result in IMD 32 delivering undesired therapy or withholding desired therapy.

In further instances, the induced energy on one or more of leads 34 and 36 may result in inadvertent stimulation or heating of the tissue and/or nerve site adjacent to any of electrodes 44, 46, 50 and 52 of respective leads 34 and 36. Such heating may result in thermal damage to the tissue adjacent the electrodes. This may in turn possibly compromise pacing and sensing thresholds at the site.

To reduce the adverse effects of disruptive energy field 11, control processor 60 may be configured to operate IMD 32 in the exposure operating mode in accordance with the selected exposure mode programming option as described in detail above. The exposure operating mode is typically less susceptible to undesirable operation in disruptive energy field 11 than the normal operating mode. In other words, operating IMD 32 in the exposure mode may reduce if not eliminate some or all of the adverse effects that disruptive energy field 11 have on therapy delivery to patient 12. When operating in the exposure operating mode, control processor 60 is configured to operate with different functionality compared to the normal operating mode. Processor 60 may, in some instances, be configured to operate with reduced functionality. For example, processor 60 may not provide sensing, not deliver therapy, delivery only a subset of possible therapies, not log collected data or the like. In other instances, processor 60 may be operating with approximately the same functionality or even increased functionality in the exposure mode. For example, processor 60 may use a different sensor or algorithm to detect cardiac activity of the heart of patient 12, such as pressure sensor measurements rather than electrical activity of the heart.

Processor 60 may receive the parameters of the exposure operating mode from a user via programming device 18. In other words, the exposure operating mode parameters may be manually configured by the user. In another example, at least a portion, and in some cases all, of the parameters of the exposure operating mode may be automatically determined One example technique for automatically determining one or more parameters of the exposure operating mode is described in co-pending patent application Ser. No. 12/569,101 to Ellingson et al., entitled, "AUTOMATIC SELECTION OF PARAMETERS OF AN EXPOSURE MODE OF AN IMPLANTABLE MEDICAL DEVICE," which was filed on Sep. 29, 2009 and which is incorporated herein by reference in its entirety. Whether the parameters were manually entered or automatically determined or both, processor 60 may store the parameters of the exposure operating mode in memory 72.

Control processor 60 may include any one or more of a microprocessor, a controller, a digital signal processor (DSP), an application specific integrated circuit (ASIC), a field-programmable gate array (FPGA), or equivalent discrete or integrated circuitry, including analog circuitry, digital circuitry, or logic circuitry. The functions attributed to control processor 60 herein may be embodied as software, firmware, hardware or any combination thereof.

Memory 72 may include computer-readable instructions that, when executed by control processor 60 or other component of IMD 32, cause one or more components of IMD 32 to perform various functions attributed to those components in this disclosure. Memory 72 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other computer-readable storage media.

The various components of IMD 32 are coupled to power source 74, which may include a rechargeable or non-rechargeable battery. A non-rechargeable battery may be capable of holding a charge for several years, while a rechargeable battery may be inductively charged from an external device, e.g., on a daily or weekly basis. Power source 74 also may include power supply circuitry for providing regulated voltages and/or current levels to power the various components of IMD 32.

Under the control of processor 60, telemetry module 70 may receive downlink telemetry from and send uplink telemetry to programming device 18 with the aid of an antenna 78, which may be internal and/or external to IMD 32. Telemetry module 70 includes any suitable hardware, firmware, software or any combination thereof for communicating with another device, such as programming device 18. For example, telemetry module 70 may include appropriate modulation, demodulation, encoding, decoding, frequency conversion, filtering, and amplifier components for transmission and reception of data.

The various modules of IMD 32 may include one or more processors, such as one or more microprocessors, digital signal processors (DSPs), application specific integrated circuits (ASICs), field-programmable gate arrays (FPGAs), programmable logic circuitry, or the like, that may perform various functions and operations, such as those described herein.

Figure 4:
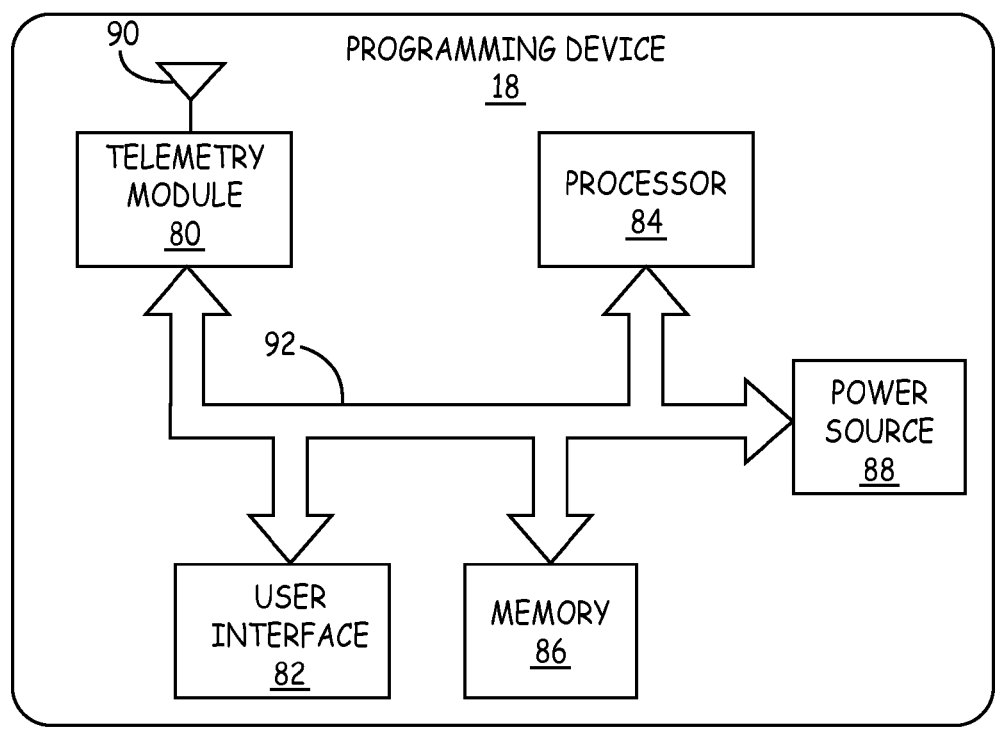
FIG. 4 is a block diagram illustrating an example programming device in further detail.

FIG. 4 is a block diagram illustrating an example programming device 18 in further detail. Programming device 18 may correspond to a programming device, a monitoring device or other external device located on or in the vicinity of patient 12. As illustrated in the example of FIG. 4, programming device 18 includes a telemetry module 80, user interface 82, control processor 84, memory 86 and power source 88, all of which are interconnected by a data bus 92.

A user (e.g., a physician) may interact with a programming device 18 to select the manner in which the exposure operating mode of IMD 32 is enabled or disabled. The user may, for example, interact with programming device 18 via user interface 82 to select one of a plurality of exposure mode programming options supported by IMD 32. User interface 82 may include an output mechanism and an input mechanism via which the user interacts. The output mechanism may, for example, include an electronic display, e.g., a cathode ray tube (CRT) display, a liquid crystal display (LCD) or light emitting diode (LED) display, and/or a speaker. The input mechanism may be a keypad, a peripheral pointing device, such as a mouse, and/or a microphone via which a user may interact with the user interface. In some embodiments, the display of programming device 18 may include a touch screen display, and a user may interact with programming device 18 via the display.

Programming device 18 may include an electronic display via which programming device 18 presents the user with one or more graphical user interfaces for use in selecting the desired exposure mode programming option for IMD 32. For example, programming device 18 may present a graphical user interface on the display that presents the programming options supported by IMD 32 for enabling and disabling the exposure operating mode. The graphical user interface may include one or more text-based hyperlinks and/or graphical or visual indicators, e.g., windows, menus, buttons, radio buttons, check boxes, text boxes, drop-down lists, icons, or the like that represent the exposure mode programming options supported by IMD 32. One such graphical user interface is illustrated and described in more detail in FIG. 8. In other instances, the user interface presented to the user may be a text-based interface, such as a command-line interface (CLI), in which text commands are used for interaction. In yet other instances, the user interface 82 may present the programming options audibly, e.g., via a speaker.

In one instance, programming device 18 may receive a communication from IMD 32 and determine the exposure mode programming options supported by IMD 32 based on the communication from IMD 32. For example, programming device 18 may maintain a mapping, e.g., in memory 86, that associates each type of IMD with corresponding exposure mode programming options supported by the IMD. In this manner, programming device 18 may determine the exposure mode programming options supported by IMD 32 based a device type, a device serial number or other information contained in a header of the communication from IMD 32. Alternatively, the sent communication from IMD 32 may include the exposure mode programming options supported by IMD 32. As such, programming device 18 may query IMD 32 to retrieve the exposure mode programming options supported by IMD 32.

The user selects, e.g., via the input mechanism, the desired programming option for enabling and disabling the exposure operating mode from the list on the graphical user interface. The desired programming option selected by the user may be based on user preference, patient preference, resource availability, experience scanning patients with IMDs, clinical practice within or across geographies, or other factor.

Figure 8:
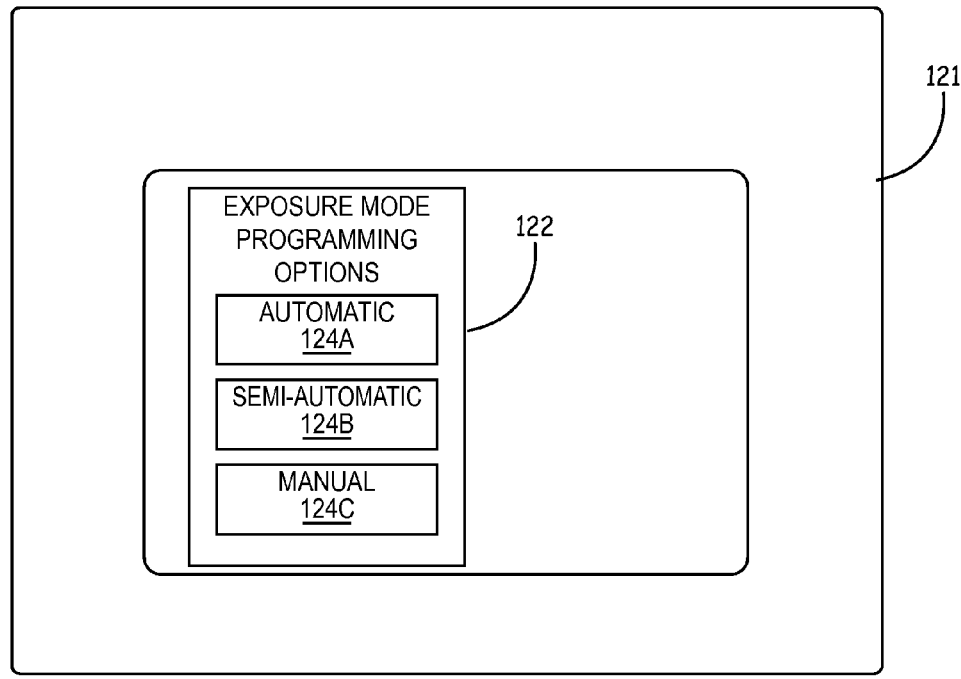
FIGS. 8-10 are conceptual diagrams illustrating example graphical user interfaces on an electronic display that allow a user to interact with the programming device to selectively configure the exposure mode programming option of an IMD.
Figure 9:
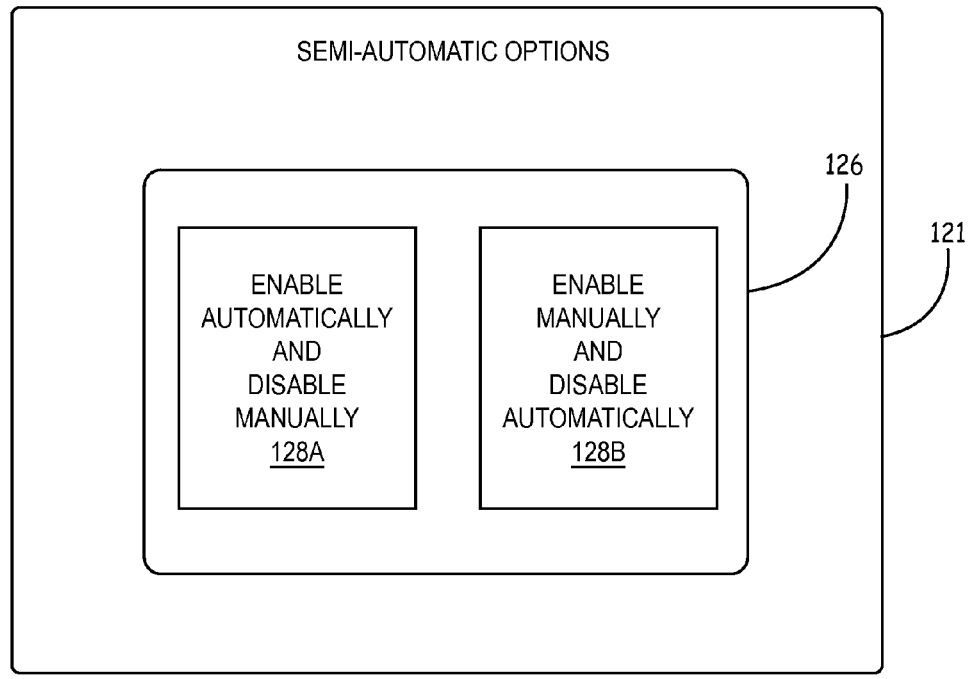
Figure 10:
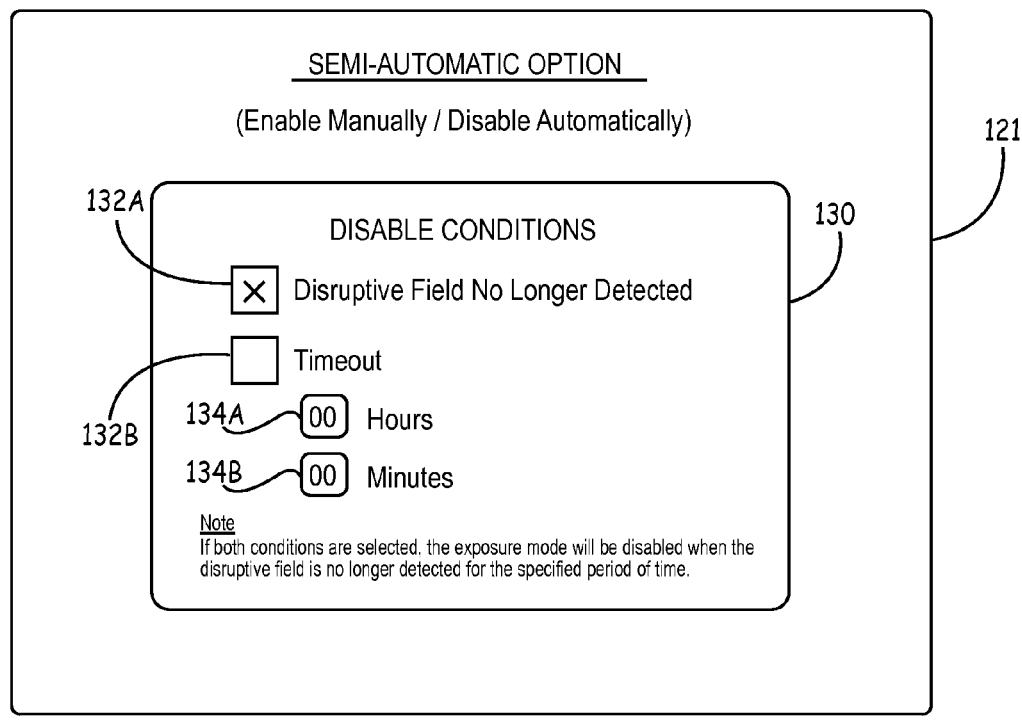

In some instances, programming device 18 may present a series of one or more additional graphical user interfaces via the display in response to the user selecting the desired exposure mode programming option. The series of additional graphical user interfaces may, for example, include a graphical user interface that presents a list of settings within the selected exposure mode programming option that the user may also configure. One example series of graphical user interfaces is illustrated in FIGS. 8-10. As another example, a second graphical user interface may present the user with the option to select conditions for enablement of the exposure operating mode or the option to select conditions for disablement of the exposure operating mode for the automatic exposure mode programming option. Within each of these options, another graphical user interface may be presented to provide the user with the ability to select the type of condition(s) (e.g., detection of disruptive energy field 11 with disruptive field detector 68, expiration of a timer, detection of some other signal, or other condition or a combination of conditions,) as well as specify thresholds for each of the conditions (e.g., threshold magnitudes of the detected fields, time periods for the timer or the like). The selected exposure programming option and/or the settings of the selected programming option may be stored within memory 86.

Programming device 18 transmits a communication to IMD 32 to configure IMD 32 into the selected exposure mode programming option and, in some instances, settings for the selected exposure programming option. Processor 84 controls telemetry module 80 to transmit the communication to telemetry module 70 of IMD 32. Telemetry module 80 communicates wirelessly with IMD 32 and, more specifically, with telemetry module 70 of IMD 32. Telemetry module 80, like telemetry module 70 of IMD 32, may include any suitable hardware, firmware, software or any combination thereof for communicating with IMD 32. For example, telemetry module 80 may include appropriate modulation, demodulation, frequency conversion, filtering, and amplifier components for transmission and reception of data, including radio frequency (RF) components and antenna 90, as applicable. In some instances, telemetry module 80 may include two or more sets of RF components, e.g., one for communication with IMD 32 and one for communication with another computing device (e.g., remote server).

The various modules of programming device 18 may include one or more processors, such as one or more microprocessors, digital signal processors (DSPs), application specific integrated circuits (ASICs), field-programmable gate arrays (FPGAs), programmable logic circuitry, or the like, that may perform various functions and operations, such as those described herein.

Figure 5:
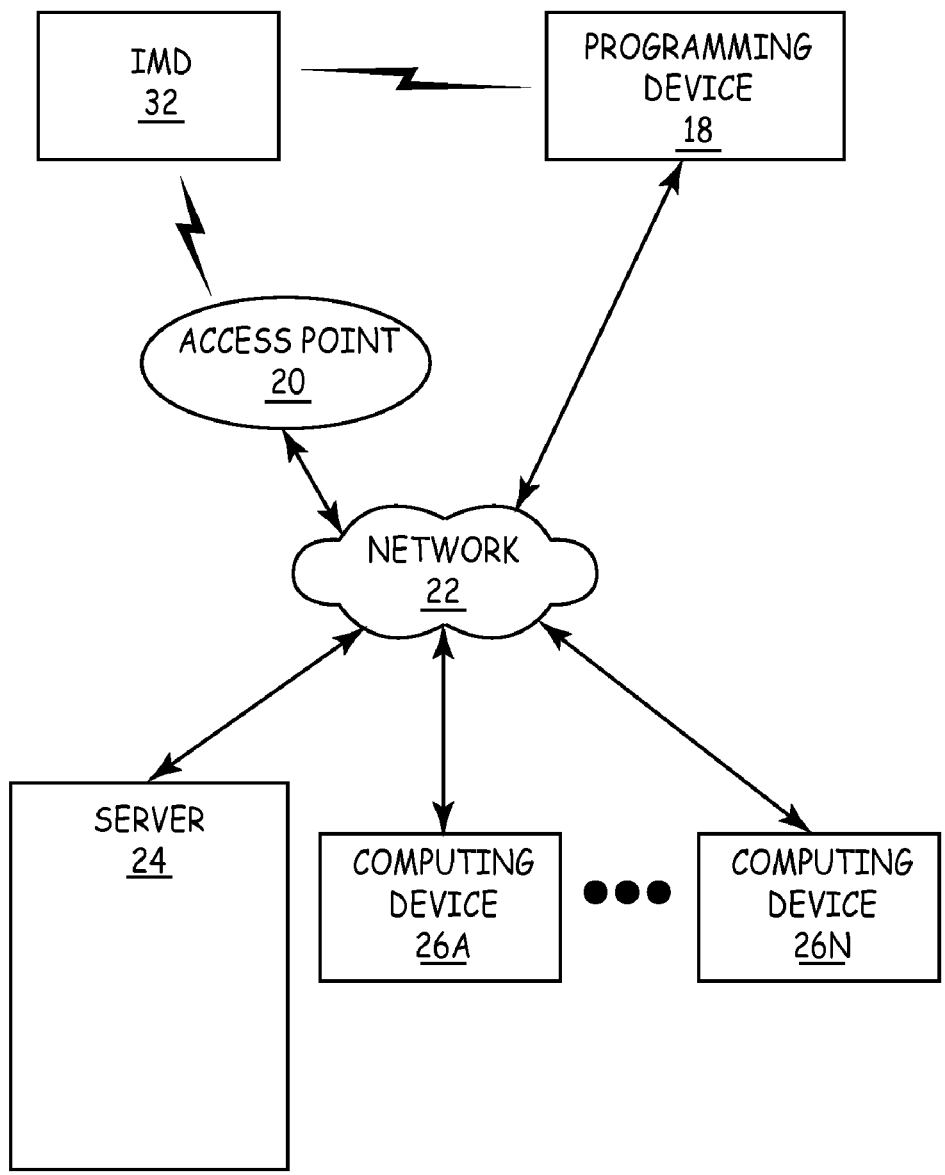
FIG. 5 is a block diagram illustrating an example system that includes an IMD, a programming device, an access point, a server and one or more computing devices interconnected via a network.

FIG. 5 is a block diagram illustrating an example system that includes IMD 32, a programming device 18, an access point 20, a network 22, a server 24 and one or more computing devices 26A-26N. In the example of FIG. 5, programming device 18, access point 20, server 24 and computing devices 26 are interconnected, and able to communicate with each other, through network 22. Programming device 18, access point 20, server 24, and computing devices 26A-26N may each include one or more processors, such as one or more microprocessors, DSPs, ASICs, FPGAs, programmable logic circuitry, or the like, that may perform various functions and operations, such as those described herein.

IMD 32 may communicate with programming device 18 via a first wireless connection and communicate with access point 20 via a second wireless connection. Programming device 18 and/or access point 20 may connect to network 22 via any of a variety of wired or wireless connections, such as telephone dial-up, digital subscriber line (DSL), cable modem connection, Infrared Data Association (IrDA), Bluetooth, IEEE 802.11, General Packet Radio Service (GPRS) or the like. As such, programming device 18 and access point 20 may forward data from IMD 32 to any other device connected to network 22.

In some embodiments, access point 20 may be co-located with patient 32 and may comprise one or more programming units and/or computing devices (e.g., one or more monitoring units) that may perform various functions and operations described herein. For example, access point 20 may include a home-monitoring unit that is co-located with patient 32 and that may monitor the activity of IMD 32. In some embodiments, server 24 or computing devices 26 may control or perform any of the various functions or operations described herein, e.g., allow a user to manually select the exposure mode programming option of IMD 32. In other words, the various user interfaces described above with respect to programming device 18 may alternatively be presented to a user remotely via one or more computing devices 26. In other words, the user (e.g., a physician) may select the exposure mode programming option to be used remotely via computing device 26 in the same manner described above in FIG. 4 with respect to programming device 18.

In some cases, server 24 may be configured to provide a secure storage site for archival of sensing integrity information that has been collected from IMD 32 and/or programming device 18. In some cases, programming device 18 or server 24 may assemble information, such as the automatically determined parameters of the exposure operating mode, in web pages or other documents for viewing by trained professionals, such as clinicians, via viewing terminals associated with computing devices 26. The system of FIG. 5 may be implemented, in some aspects, with general network technology and functionality similar to that provided by the Medtronic CareLink® Network developed by Medtronic, Inc., of Minneapolis, Minn.

Figure 6:
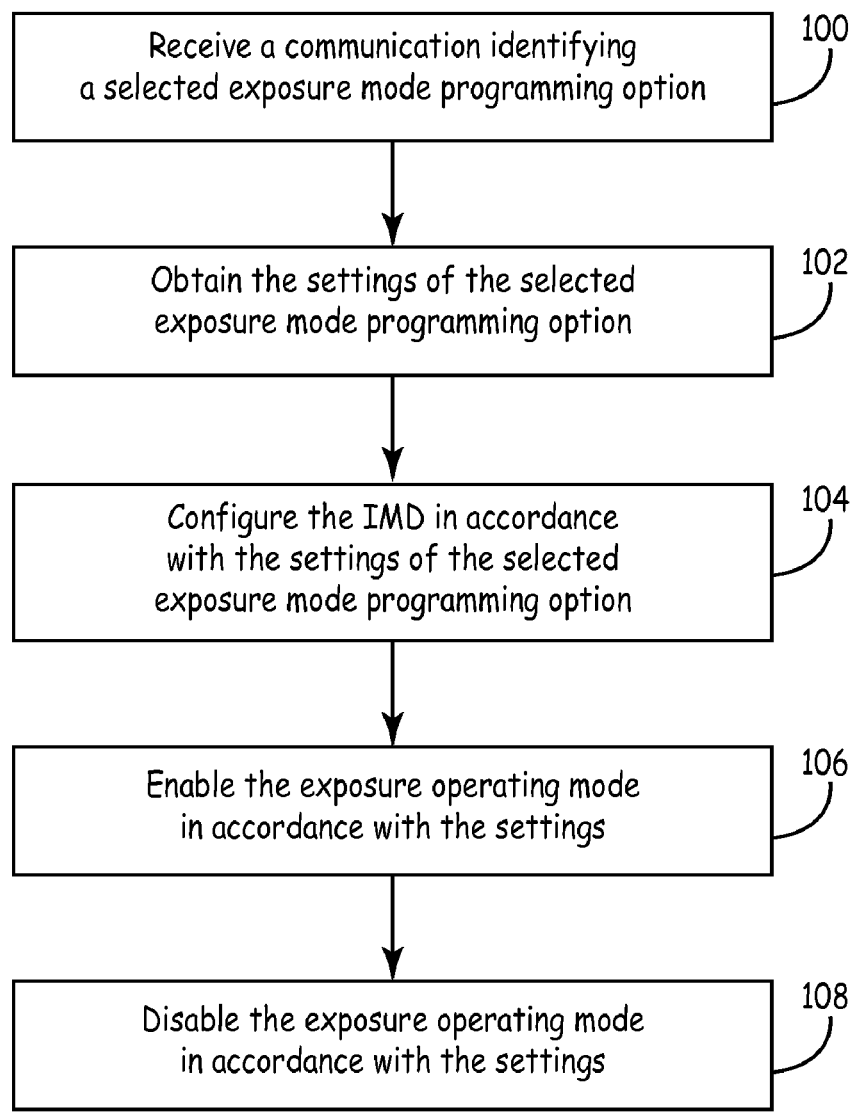
FIG. 6 is a flow diagram illustrating example operation of selectively configuring an exposure mode programming option of an IMD in accordance with one aspect of this disclosure.

FIG. 6 is a flow diagram illustrating example operation of an IMD, such as IMD 14 or 32, in accordance with one aspect of this disclosure. Processor 60 of IMD 32 receives a communication indicating an exposure mode programming option selected by a user, e.g., a physician (100). The communication may be a wireless telemetry communication received via any of a number of wireless communication protocols as described in detail above. The selected exposure mode programming option may be indicated in the header or payload of the communication.

Processor 60 obtains the settings of the selected exposure mode programming option (102). Processor 60 may store predetermined configuration settings for each of the programming options in memory 72 and obtain the configuration settings corresponding to the selected programming option from memory 72. Alternatively, the communication signal received by processor 60 may include the configuration settings for the programming option selected by the user. Thus, processor 60 may obtain the configuration settings for the programming options from the communication signal itself. The configuration settings of the programming option may include, for example, conditions to monitor for (e.g., detection of disruptive energy field 11 or expiration of a time period) as well as thresholds to use in monitoring for the conditions. The configuration settings of the programming option may, however, include a number of other settings for the programming option.

Processor 60 configures IMD 32 in accordance with the settings of the selected exposure mode programming option (104). For the manual exposure mode programming option, processor 60 may be configured to disregard the output of disruptive field detector 68 and the timer (not shown) since the manual programming option requires that the exposure operating mode be manually enabled and manually disabled, e.g., via interaction with programming device 18.

For the automatic exposure mode programming option, processor 60 may be configured to monitor disruptive field detector 68, a timer, or the output of some other sensor or detector in determining whether to enable and disable the exposure operating mode. In this manner, processor 60 is configured to automatically enable and automatically disable the exposure operating mode in response to one or more conditions, e.g., detection of disruptive energy field 11 with disruptive field detector 68 (e.g., detection of the static magnetic field, the gradient magnetic fields or the RF pulses of MRI scanner 16), expiration of a timer, detection of some other signal, or other condition or a combination of conditions. As described above, processor 60 may be configured to monitor for the same condition(s) for enabling and disabling the exposure operating mode or monitor for different condition(s) for enabling the exposure operating mode than the condition(s) for disabling the exposure operating mode.

For the semi-automatic exposure mode programming option, processor 60 may be configured to disregard the output of disruptive field detector 68, timer, or other sensor/detector for enabling the exposure operating mode and be configured to monitor disruptive field detector 68, a timer, and/or an output of some other sensor/detector for disabling the exposure operating mode. Alternatively, processor 60 may be configured to monitor the output of disruptive field detector 68, timer, or other sensor/detector for enabling the exposure operating mode and be configured to disregard the output of disruptive field detector 68, the timer, and/or an output of some other sensor/detector for disabling the exposure operating mode.

Processor 60 of IMD 32 enables the exposure operating mode in accordance with the settings of the programming option (106). Processor 60 may, for example, enable the exposure operating mode in response to receiving a communication from programming device 18 when configured in the manual programming option or enable the exposure operating mode in response to detecting one or more conditions when configured in the automatic programming option.

Processor 60 of IMD 32 disables the exposure operating mode in accordance with the settings of the programming option (108). Processor 60 may, for example, disable the exposure operating mode in response to receiving a communication from programming device 18 when configured in the manual programming option or disable the exposure operating mode in response to detecting one or more conditions when configured in the automatic programming option.

Figure 7:
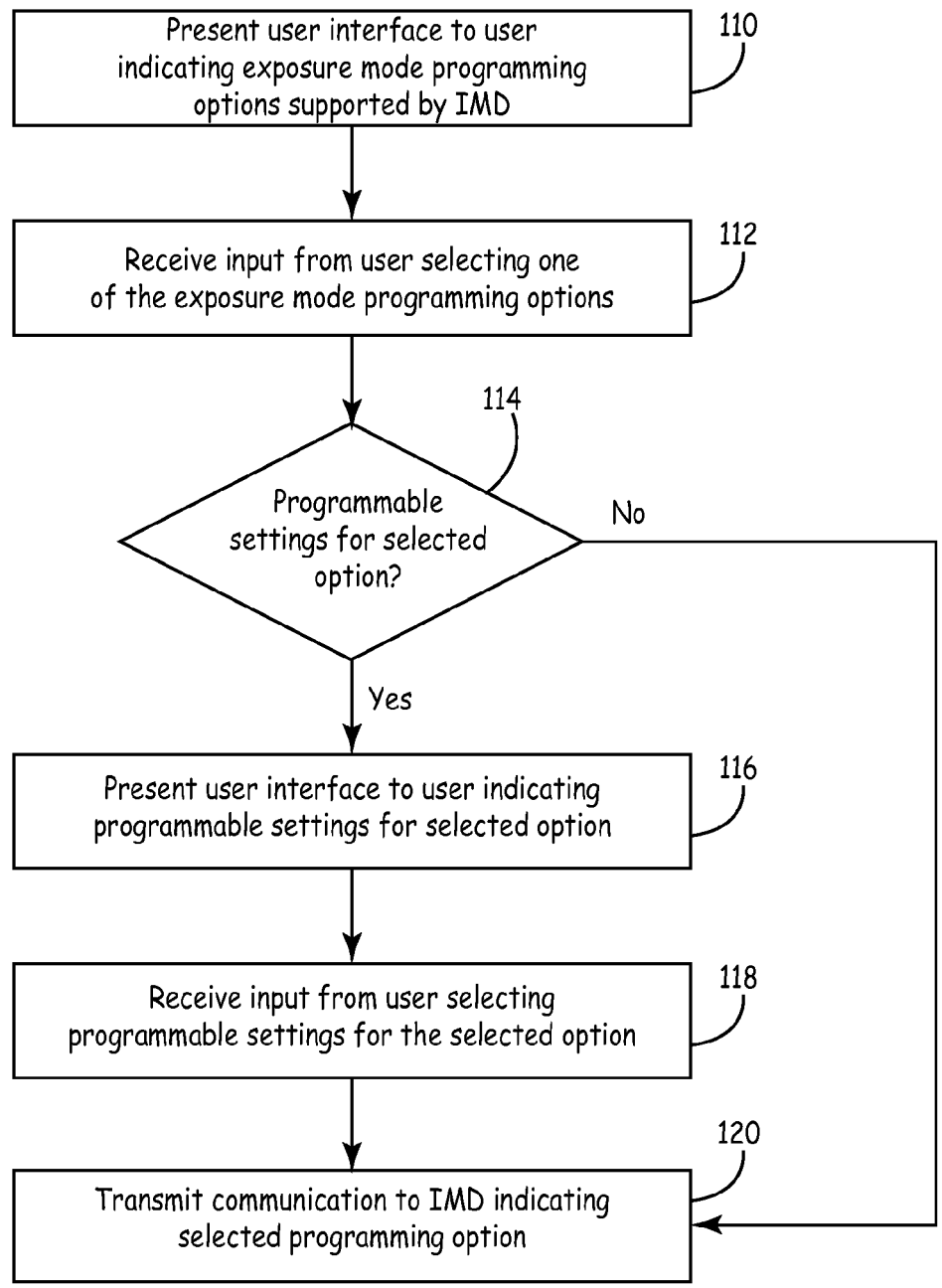
FIG. 7 is a flow diagram illustrating example operation of a programming device interacting with a user to selectively configure an exposure mode programming option of an IMD in accordance with one aspect of this disclosure.

FIG. 7 is a flow diagram illustrating example operation of an IMD, such as IMD 14 or 32, in accordance with one aspect of this disclosure. Processor 84 of programming device 18 presents the programming options supported by IMD 32 for enabling and disabling the exposure operating mode via an output mechanism of user interface 82 (110). As described above, the output mechanism may be a electronic display via which processor 84 presents a graphical user interface that may include one or more text-based hyperlinks, graphical icons and/or or visual indicators that present the exposure mode programming options supported by IMD 32. As another example, the output mechanism may be a speaker that audibly presents the programming options supported by IMD 32.

Processor 84 receives input from the user selecting the desired programming option for enabling and disabling the exposure operating mode (112). Processor 84 may receive input from the user via the input mechanism, which may be a keypad, peripheral device, touch screen or microphone. Processor 84 may determine whether the selected programming option has any programmable settings (114). When the selected programming option has programmable settings ("YES" branch of 114), processor 84 may present one or more additional graphical user interfaces to the user indicating settings for the selected programming option (116). When the selected programming option is the automatic programming option or the semi-automatic programming option, for example, processor 84 may present one or more graphical user interfaces to allow the user to set the types and/or number of conditions to automatically enable and/or automatically disable the exposure operating mode, select particular threshold values for each of the selected condition or conditions, or the like.

Processor 84 receives input from the user via user interface 82 (which includes a key pad, peripheral pointing device or touch screen) selecting programmable settings for the selected programming option (118). The selected programming option and the settings selected by the user may be stored within memory 86 of programming device 18.

After receiving the input from the user programming the settings for the selected programming option or when the selected programming option does not have any programmable settings, or the user does not want to program the settings ("NO" branch of 114), programming device 18 transmits a communication to IMD 32 to configure IMD 32 into the selected exposure mode programming option and, in some instances, configuring the settings for the selected exposure programming option (120). In this manner, the user may interact with programming device 18 to selectively configure the exposure mode programming option of IMD 32. As such, an exposure mode programming option may be selectable by a user, e.g., a physician, based on physician preference, patient preference, resource availability, experience scanning patients with IMDs, clinical practice within or across geographies, or other factor.

FIGS. 8-10 are conceptual diagrams illustrating example graphical user interfaces on a display 121 that allow a user to interact with programming device 18 to select the exposure mode programming option and, in some instances, settings within the selected exposure mode programming option. The graphical user interfaces of FIGS. 8-10 are one example of a series of graphical user interfaces presented to the user. In particular, the graphical user interface of FIG. 8 may initially be presented to the user, the graphical user interface of FIG. 9 may be presented to the user in response to the user selecting the semi-automatic programming option of the graphical user interface of FIG. 8, and the graphical user interface of FIG. 10 may be presented to the user in response to the user selecting the enable manually and disable automatically setting of the graphical user interface of FIG. 9.

FIG. 8 is a conceptual diagram of an example graphical user interface on a display 121 that may be presented by programming device 18 to the user in accordance with the techniques of this disclosure. The graphical user interface includes a window 122 and buttons 124A-124C within window 122 that presents the user with the exposure mode programming options supported by IMD 32. In the example illustrated in FIG. 8, button 124A represents the automatic exposure mode programming option, button 124B represents the semi-automatic exposure mode programming option, and button 124C represents the manual exposure mode programming option.

The user may interact with the graphical user interface via user interface 82 (e.g., keypad, peripheral pointing device or touch screen display) to select one of the buttons 124A-124C and thereby choose the desired exposure mode programming option. For purposes of discussion, it will be assumed that the user selected button 124B corresponding to the semi-automatic programming option. In response to selecting button 124B, processor 84 presents the graphical user interface illustrated in FIG. 9.

The graphical user interface of FIG. 9 includes a window 126 and buttons 128A and 128B. Button 128A corresponds with the semi-automatic programming option in which the exposure operating mode is automatically enabled (e.g., in response to detecting disruptive energy field 11) and manually disabled (e.g., in response to a communication from programming device 18). Button 128B corresponds with the semi-automatic programming option in which the exposure operating mode is manually enabled and automatically disabled. The user may interact with the graphical user interface via user interface 82 (e.g., keypad, peripheral pointing device or touch screen display) to select one of the buttons 128A and 128B and thereby choose the desired semi-automatic programming option for IMD 32. For purposes of discussion, it will be assumed that the user selected button 128B corresponding to the semi-automatic programming option in which the exposure operating mode is manually enabled and automatically disabled. In response to selecting button 128B, processor 84 presents the graphical user interface illustrated in FIG. 10 indicating settings for the selected programming option.

The graphical user interface of FIG. 10 includes a window 130, check boxes 132A and 132B, and text boxes 134A and 134B. Each of check boxes 132A and 132B corresponds with a condition for automatically disabling the exposure operating mode. In the example illustrated in FIG. 10, check box 132A corresponds with the condition of detecting disruptive energy field 11 (e.g., using disruptive field detector 68) and check box 132B corresponds with the condition of expiration of a timer. Other check boxes may be included for other conditions. For each of the conditions, the graphical user interface may include one or more text boxes, such as text boxes 134A and 134B, for entering threshold values for the respective conditions. In the example illustrated in FIG. 10, text boxes 134A and 134B provide the user the capability to enter a threshold period of time for the timer by specifying the amount of time in hours and minutes, respectively. Window 130 may also include one or more notes, such as the note indicating to the user that if both conditions are selected, the exposure operating mode will be disabled when the disruptive field is no longer detected for the specified period of time. In the example illustrated in FIG. 11, the user has selected only one disable condition, i.e., the disruptive energy field no longer being detected. However, the user may select more than one disable condition.

The graphical user interfaces of FIGS. 8-10 are provided for purposes of illustration and should not be considered limiting of the type, number or layout of graphical user interfaces that may be used in accordance with the techniques of this disclosure. Moreover, the series of graphical user interfaces is only one example of the order of graphical user interfaces that may be presented to the user. A different series of graphical user interfaces may be presented to the user in the case of the manual programming option or the automatic programming option. Although shown as taking up a large portion of the display, the graphical user interfaces may be located within smaller portions of the display, e.g., along the side or in the corner of the display, and other information and data may be displayed concurrently with the illustrated graphical user interfaces.

The techniques described in this disclosure, including those attributed to IMD 14 and/or 32, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, SRAM, EEPROM, flash memory, magnetic data storage media, optical data storage media, or the like. The instructions may be executed to support one or more aspects of the functionality described in this disclosure.

Various examples have been described. These and other examples are within the scope of the following claims.

The invention claimed is:

1. An implantable medical device comprising:
    a memory configured to store parameters of an exposure operating mode and to store configuration settings of a plurality of exposure mode programming options, wherein the configuration settings for each of the plurality of exposure mode programming options define a manner for enabling and disabling the exposure operating mode;
    a receiver configured to receive a communication from an external medical device, wherein the communication identifies one of the plurality of exposure mode programming options; and
    a processor configured to obtain the configuration settings of the one of the plurality of exposure mode programming options identified in the communication received by the receiver, to enable the exposure operating mode in accordance with the obtained configuration settings of the identified exposure mode programming option and to disable the exposure operating mode in accordance with the obtained configured settings of the identified exposure mode programming option.

2. The implantable medical device of claim 1, wherein the configuration settings of the plurality of exposure mode programming options define at least two of:
    a manual exposure mode programming option in which the processor is configured to enable and disable the exposure operating mode in response to a communication from the external device,
    an automatic exposure mode programming option in which the processor is configured to automatically enable and disable the exposure operating mode in response to detecting one or more conditions,
    a semi-automatic exposure mode programming option in which the processor is configured to automatically enable the exposure operating mode in response to detecting one or more conditions and to disable the exposure operating mode in response to a communication from the external device, and
    a semi-automatic exposure mode programming option in which the processor is configured to enable the exposure operating mode in response to a communication from the external device and to automatically disable the exposure operating mode in response to detecting one or more conditions.

3. The implantable medical device of claim 2, wherein the one or more conditions comprise at least one of detecting a magnetic resonance imaging (MRI) environment, detecting a disruptive energy field, and expiration of a timer.

4. The implantable medical device of claim 1, wherein the communication comprises a first communication and further wherein:
    the receiver is configured to receive a second communication, wherein the second communication identifies a second one of the plurality of exposure mode programming options; and
    the processor is configured to obtain the configuration settings of the second one of the plurality of exposure mode programming options identified in the second communication received by the receiver, to enable the exposure operating mode in accordance with the obtained configuration settings of the second one of the exposure mode programming options and to disable the exposure operating mode in accordance with the obtained configuration settings of the second one of the exposure mode programming options.

5. The implantable medical device of claim 1, further comprising a transmitter configured to send a communication to the external device to identify the plurality of exposure mode programming options supported by the implantable medical device.

6. The implantable medical device of claim 1, further comprising a disruptive field detector configured to detect a disruptive energy field, wherein the configuration settings of the identified exposure mode programming option includes at least one of automatically enabling the exposure operating mode in response to disruptive field detector detecting the disruptive energy field and automatically disabling the exposure operating mode in response to no longer detecting the disruptive energy field.

7. A method comprising:
    storing parameters of an exposure operating mode;
    storing configuration settings of a plurality of exposure mode programming options, wherein the configuration settings for each of the plurality of exposure mode programming options define a manner for enabling and disabling the exposure operating mode;
    receiving a communication from an external medical device, wherein the communication identifies one of the plurality of exposure mode programming options;
    configuring an implantable medical device to operate in the one of the plurality of exposure mode programming options identified in the received communication;
    enabling the exposure operating mode in accordance with the configuration settings of the identified exposure mode programming option; and
    disabling the exposure operating mode in accordance with the configuration settings of the identified exposure mode programming option.

8. The method of claim 7, wherein the configuration settings of the plurality of exposure mode programming options define at least two of:
    a manual exposure mode programming option in which the exposure operating mode is manually enabled and manually disabled via communication with the external device,
    an automatic exposure mode programming option in which the exposure operating mode is automatically enabled and automatically disabled in response to detecting one or more conditions,
    a semi-automatic exposure mode programming option in which the exposure operating mode is automatically enabled in response to detecting one or more conditions and manually disabled via communication with the external device, and a semi-automatic exposure mode programming option in which the exposure operating mode is manually enabled via communication with the external device and automatically disabled in response to detecting one or more conditions.

9. The method of claim 8, wherein the one or more conditions comprise at least one of detecting a magnetic resonance imaging (MRI) environment, detecting a disruptive energy field, and expiration of a timer.

10. The method of claim 7, wherein the communication comprises a first communication, the method further comprising:
receiving a second communication, wherein the second communication identifies a second one of the plurality of exposure mode programming options;
configuring the implantable medical device to operate in the second one of the plurality of exposure mode programming options identified in the second communication;
enabling the exposure operating mode in accordance with the configuration settings of the identified second one of the exposure mode programming options; and
disabling the exposure operating mode in accordance with the configuration settings of the identified second one of the exposure mode programming options.

11. The method of claim 7, further comprising transmitting a communication to the external device to identify the plurality of exposure mode programming options supported by the implantable medical device.

12. A device comprising:
means for storing parameters of an exposure operating mode and configuration settings of a plurality of exposure mode programming options, wherein the configuration settings for each of the plurality of exposure mode programming options define a manner for enabling and disabling the exposure operating mode;
means for receiving a communication from an external medical device;
means for configuring an implantable medical device to operate in accordance with the configuration settings of one of the plurality of exposure mode programming options based on the received communication;
means for enabling the exposure operating mode in accordance with the configuration settings of the one of the plurality of exposure mode programming options in which the implantable medical device is configured to operate; and
means for disabling the exposure operating mode in accordance with the configuration settings of the one of the plurality of exposure mode programming options in which the implantable medical device is configured to operate.

13. The device of claim 12, wherein the stored configuration settings define at least two of:
a manual exposure mode programming option in which the exposure operating mode is manually enabled and manually disabled via communication with the external device,
an automatic exposure mode programming option in which the exposure operating mode is automatically enabled and automatically disabled in response to detecting one or more conditions,
a semi-automatic exposure mode programming option in which the exposure operating mode is automatically enabled in response to detecting one or more conditions and manually disabled via communication with the external device, and
a semi-automatic exposure mode programming option in which the exposure operating mode is manually enabled via communication with the external device and automatically disabled in response to detecting one or more conditions.

14. The device of claim 13, wherein the one or more conditions comprise at least one of detecting a magnetic resonance imaging (MRI) environment, detecting a disruptive energy field, and expiration of a timer.

15. The device of claim 12, wherein the communication comprises a first communication, and further wherein:
the means for receiving receives a second communication;
the means for configuring configures the implantable medical device to operate in accordance with the configuration settings of a second one of the plurality of exposure mode programming options based on the second communication;
the means for enabling enables the exposure operating mode in accordance with the configuration settings of the second one of the plurality of exposure mode programming options; and
the means for disabling disables the exposure operating mode in accordance with the configuration settings of the second one of the plurality of exposure mode programming options.

16. The device of claim 12, further comprising means for transmitting a communication to the external device to identify the plurality of exposure mode programming options supported by the implantable medical device.

17. A non-transitory computer-readable storage medium that stores parameters of an exposure operating mode and configuration settings of a plurality of exposure mode programming options, wherein the configuration settings for each of the plurality of exposure mode programming options define a manner for enabling and disabling the exposure operating mode, the computer-readable storage medium comprising instructions that, when executed, cause an implantable medical device to:
receive a communication from an external medical device;
configure an implantable medical device to operate in accordance with the configuration settings of one of a plurality of exposure mode programming options based on the received communication;
enable the exposure operating mode in accordance with the configuration settings of the one of the plurality of exposure mode programming options; and
disable the exposure operating mode in accordance with the configuration settings of the one of the plurality of exposure mode programming options.

18. The non-transitory computer-readable storage medium of claim 17, further comprising instructions that, when executed, cause the implantable medical device to:
receive a second communication;
configure the implantable medical device to operate in accordance with the configuration settings of a second one of the plurality of exposure mode programming options based on the second communication;
enable the exposure operating mode in accordance with the configuration settings of the second one of the exposure mode programming options; and
disable the exposure operating mode in accordance with the configuration settings of the second one of the exposure mode programming options.

19. The non-transitory computer-readable storage medium of claim 17, further comprising instructions that, when executed, cause the implantable medical device to transmit a communication to the external device to identify the plurality of exposure mode programming options supported by the implantable medical device.

* * * * *